United States Patent
Jungkamp et al.

(10) Patent No.: US 7,538,240 B2
(45) Date of Patent: May 26, 2009

(54) METHOD FOR THE HYDROCYANATION OF BUTADIENE

(75) Inventors: Tim Jungkamp, Kapellen (BE); Robert Baumann, Mannheim (DE); Michael Bartsch, Neustadt (DE); Gerd Haderlein, Grünstadt (DE); Hermann Luyken, Ludwigshafen (DE); Jens Scheidel, Hirschberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 519 days.

(21) Appl. No.: 10/587,026

(22) PCT Filed: Jan. 27, 2005

(86) PCT No.: PCT/EP2005/000780

§ 371 (c)(1),
(2), (4) Date: Jul. 24, 2006

(87) PCT Pub. No.: WO2005/073173

PCT Pub. Date: Aug. 11, 2005

(65) Prior Publication Data

US 2008/0242883 A1    Oct. 2, 2008

(30) Foreign Application Priority Data

Jan. 29, 2004    (DE)    ................. 10 2004 004 673

(51) Int. Cl.
*C07C 255/01*    (2006.01)
(52) U.S. Cl. ...................................... 558/308; 558/335
(58) Field of Classification Search .................. None
See application file for complete search history.

(56) References Cited

U.S. PATENT DOCUMENTS 3,850,973 A    11/1974    Seidel et al.
6,169,198 B1    1/2001    Fischer et al.

FOREIGN PATENT DOCUMENTS

WO    WO-99/07671    2/1999

OTHER PUBLICATIONS

Casalnuovo et al., 1994. "Ligand Electronic Effects in Asymmetric Catalysis: Enhanced Enantioselectivity in the Asymmetric Hydrocyanation of Vinylarenes" *Journal of the American Chemical Society* 116, 9869-9882.
W. Broetz, A. Schonbucher. 1982 Technische Chemie I p. 157, 158, 246, 247.

*Primary Examiner*—Kamal A Saeed
(74) *Attorney, Agent, or Firm*—Connolly Bove Lodge & Hutz LLP

(57) ABSTRACT

A process is described for preparing 3-pentenenitrile by hydrocyanating 1,3-butadiene in the presence of at least one catalyst, wherein the reaction is carried out in a loop reactor having external pumped circulation and jet nozzle for driving the internal circulation.

13 Claims, No Drawings

METHOD FOR THE HYDROCYANATION OF BUTADIENE

CROSS REFERENCE TO RELATED APPLICATIONS

This application is a National Phase of PCT/EP2005/000780, filed Jan. 27, 2005, which claim priority to German application 102004004673.5 filed Jan. 29, 2004.

DESCRIPTION

The present invention relates to a process for preparing 3-pentenenitrile by hydrocyanating 1,3-butadiene in the presence of at least one catalyst.

Adiponitrile is an important starting material in nylon production and is obtained by double hydrocyanation of 1,3-butadiene. In a first hydrocyanation, 1,3-butadiene is hydrocyanated to 3-pentenenitrile. In a second, subsequent hydrocyanation, 3-pentenenitrile is reacted with hydrogen cyanide to adiponitrile. Both hydrocyanations are catalyzed by nickel(0)-phosphorus complexes.

When the concentration of hydrogen cyanide during the hydrocyanation of 1,3-butadiene is too high, the result is formation of nickel(II) cyanides. The formation of these nickel(II) salts is attributable to oxidation of the nickel(0) catalyst with hydrogen cyanide.

In J. Am. Chem. Soc. 116, page 9869 (1994), Casalnuovo describes a reaction mechanism for the hydrocyanation of olefins with formation of nickel(II) cyanide by oxidation of the nickel(0) catalyst with hydrogen cyanide in a parallel reaction.

From the existing processes for preparing 3-pentenenitrile, it is not known how the concentration of hydrogen cyanide during the hydrocyanation of 1,3-butadiene can be kept sufficiently low that, on the one hand, a sufficient reaction rate of the hydrocyanation is ensured and, on the other, the formation of nickel(II) cyanides can be avoided.

It is thus an object of the present invention to provide a process for preparing 3-pentenenitrile by hydrocyanating 1,3-butadiene in the presence of at least one catalyst, in which a sufficient hydrocyanation rate is achieved and the formation of nickel(II) cyanides is simultaneously avoided.

The achievement of this object starts from a process for preparing 3-pentenenitrile by hydrocyanating 1,3-butadiene in the presence of at least one catalyst. In the process according to the invention, the hydrocyanation is carried out in a loop reactor having at least one feed line and at least one discharge line, an external pumped circulation system, an inlet tube and at least one jet nozzle for driving the internal circulation. The pumped circulation generates the necessary starting pressure for the nozzle spraying through the jet nozzle. In a preferred embodiment, the pumped circuit is configured in such a way that the volume of the pipelines and apparatus in the pumped circulation system can be utilized as a postreaction zone.

Owing to the shorter mixing-in times and the associated minor extent of local excess concentrations of hydrogen cyanide, the use of a loop reactor in a hydrocyanation of 1,3-butadiene is advantageous, because the nickel cyanide formation rate decreases with the product formation rate.

In one embodiment of the present invention, the process according to the invention is carried out continuously.

In a further embodiment of the present invention, the process according to the invention is carried out in the liquid phase. Therefore, the pressure in the reactor is preferably adjusted in such a way that the reactants are in liquid form at the reaction temperature used. It is also preferred that the 1,3-butadiene and the hydrogen cyanide are used in liquid form in the process according to the invention.

In a further embodiment of the process according to the invention, the loop reactor is in flooded operation. A flooded mode means that the nozzle spraying is effected into the liquid phase, and a gas phase in the reactor is not mixed in, so that there is no significant proportion of gas phase in the reaction volume, preferably no gas phase, and preferably no gas phase in the interior of the loop reactor. A flooded mode is preferred in the process according to the invention since, in a biphasic mode, 1,3-butadiene is depleted in the liquid phase. Hydrogen cyanide is thus enriched and nickel(II) cyanide is formed to an increased extent.

For hydrocyanations, one or more reactors are used and are preferably connected in series where a plurality of reactors is used.

In one embodiment of the process according to the invention, one or more further reactors are used in addition to the loop reactor, in which case at least two reactors are connected in series, hydrogen cyanide is introduced into more than one reactor, and 1,3-butadiene and the at least one catalyst are introduced into the first of the reactors connected in series.

In one embodiment of the process according to the invention, only one reactor is used, into which hydrogen cyanide, 1,3-butadiene and the at least one catalyst are metered.

In the process according to the invention, one or more of these reactors may be loop reactors, more preferably reactors into which hydrogen cyanide is introduced.

1,3-Butadiene, the at least one catalyst and hydrogen cyanide may be metered via separate feeds into the inner loop of the loop reactor used in accordance with the invention. Hydrogen cyanide is metered preferably via a jet nozzle. The loop reactor used in the process according to the invention is more preferably equipped with a nozzle which has a feed for hydrogen cyanide and a feed for the external circulation stream. This provides the possibility that 3-pentenenitrile can be withdrawn as the reaction product of the reactor at the point where the internal circulation stream has the longest circulation time before it is mixed with the driving jet.

In addition, it is preferred that the hydrogen cyanide is conducted within an internal inlet tube and the pumped circulation stream is conducted coaxially around this inlet tube, since this provides very good mixing of the reactants without local excess concentrations of hydrogen cyanide relative to the at least one catalyst present in the pumped circulation stream. These excess concentrations would lead in turn to an increased formation rate of nickel(II) cyanide compounds.

In a further embodiment of the process according to the invention, the 1,3-butadiene and/or the at least one catalyst are metered into the external pumped circuit of the loop reactor.

In a further embodiment of the process according to the invention, the loop reactor used in the process according to the invention has a vertical construction and the nozzle is installed at the top.

The inlet point for metering hydrogen cyanide into the loop reactor is preferably cooled.

In order to prevent fouling in downstream process stages, it is preferred that a postreactor is connected downstream of the loop reactor and preferably has tubular characteristics.

The process according to the invention comprises the reaction of 1,3-butadiene with hydrogen cyanide over at least one catalyst. The catalysts used are nickel(0) catalyst complexes.

The Ni(0) complexes which contain phosphorus ligands and/or free phosphorus ligands are preferably homogeneously dissolved nickel(0) complexes.

The phosphorus ligands of the nickel(0) complexes and the free phosphorus ligands are preferably selected from mono- or bidentate phosphines, phosphites, phosphinites and phosphonites.

These phosphorus ligands preferably have the formula I:

P(X¹R¹)(X²R²)(X³R³)      (I)

In the context of the present invention, compound I is a single compound or a mixture of different compounds of the aforementioned formula.

According to the invention, $X^1$, $X^2$, $X^3$ each independently are oxygen or a single bond. When all of the $X^1$, $X^2$ and $X^3$ groups are single bonds, compound I is a phosphine of the formula $P(R^1R^2R^3)$ with the definitions of $R^1$, $R^2$ and $R^3$ specified in this description.

When two of the $X^1$, $X^2$ and $X^3$ groups are single bonds and one is oxygen, compound I is a phosphinite of the formula $P(OR^1)(R^2)(R^3)$ or $P(R^1)(OR^2)(R^3)$ or $P(R^1)(R^2)(OR^3)$ with the definitions of $R^1$, $R^2$ and $R^3$ specified hereinbelow.

When one of the $X^1$, $X^2$ and $X^3$ groups is a single bond and two are oxygen, compound I is a phosphonite of the formula $P(OR^1)(OR^2)(R^3)$ or $P(R^1)(OR^2)(OR^3)$ or $P(OR^1)(R^2)(OR^3)$ with the definitions of $R^1$, $R^2$ and $R^3$ specified in this description.

In a preferred embodiment, all $X^1$, $X^2$ and $X^3$ groups should be oxygen, so that compound I is advantageously a phosphite of the formula $P(OR^1)(OR^2)(OR^3)$ with the definitions of $R^1$, $R^2$ and $R^3$ specified hereinbelow.

According to the invention, $R^1$, $R^2$, $R^3$ are each independently identical or different organic radicals. $R^1$, $R^2$ and $R^3$ are each independently alkyl radicals preferably having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, preferably having from 1 to 20 carbon atoms, such as 1,1'-biphenol, 1,1'-binaphthol. The $R^1$, $R^2$ and $R^3$ groups may be bonded together directly, i.e. not solely via the central phosphorus atom. Preference is given to the $R^1$, $R^2$ and $R^3$ groups not being bonded together directly.

In a preferred embodiment, $R^1$, $R^2$ and $R^3$ groups are radicals selected from the group consisting of phenyl, o-tolyl, m-tolyl and p-tolyl. In a particularly preferred embodiment, a maximum of two of the $R^1$, $R^2$ and $R^3$ groups should be phenyl groups.

In another preferred embodiment, a maximum of two of the $R^1$, $R^2$ and $R^3$ groups should be o-tolyl groups.

Particularly preferred compounds I which may be used are those of the formula I a

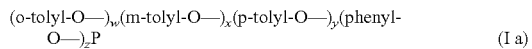

(o-tolyl-O—)$_w$(m-tolyl-O—)$_x$(p-tolyl-O—)$_y$(phenyl-O—)$_z$P      (I a)

where w, x, y and z are each a natural number and the following conditions apply: w+x+y+z=3 and w, z≦2.

Such compounds I a are, for example (p-tolyl-O—)(phenyl-O—)$_2$P, (m-tolyl-O—)(phenyl-O—)$_2$P, (o-tolyl-O—)(phenyl-O—)$_2$P, (p-tolyl-O—)$_2$(phenyl-O—)P, (m-tolyl-O—)$_2$(phenyl-O—)P, (o-tolyl-O—)$_2$(phenyl-O—)P, (m-tolyl-O—)(p-tolyl-O—)(phenyl-O—)P, (o-tolyl-O—)(p-tolyl-O)(phenyl-O—)P, (o-tolyl-O—)(m-tolyl-O—)(phenyl-O—)P, (p-tolyl-O—)$_3$P, (m-tolyl-O—)(p-tolyl-O—)$_2$P, (o-tolyl-O—)(p-tolyl-O—)$_2$P, (m-tolyl-O—)$_2$(p-tolyl-O—)P, (o-tolyl-O—)$_2$(p-tolyl-O—)P, (o-tolyl-O—)(m-tolyl-O—)(p-tolyl-O—)P, (m-tolyl-O—)$_3$P, (o-tolyl-O—)(m-tolyl-O—)$_2$P, (O-tolyl-O—)$_2$(m-tolyl-O—)P or mixtures of such compounds.

For example, mixtures comprising (m-tolyl-O—)$_3$P, (m-tolyl-O—)$_2$(p-tolyl-O—)P, (m-tolyl-O—)(p-tolyl-O—)$_2$P and (p-tolyl-O—)$_3$P may be obtained by reacting a mixture comprising m-cresol and p-cresol, in particular in a molar ratio of 2:1, as obtained in the distillative workup of crude oil, with a phosphorus trihalide, such as phosphorus tri-chloride.

In another, likewise preferred embodiment, the phosphorus ligands are the phosphites, described in detail in DE-A 199 53 058, of the formula I b:

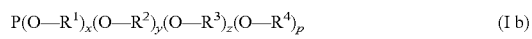

P(O—R¹)$_x$(O—R²)$_y$(O—R³)$_z$(O—R⁴)$_p$      (I b)

where $R^1$: aromatic radical having a $C_1$-$C_{18}$-alkyl substituent in the o-position to the oxygen atom which joins the phosphorus atom to the aromatic system, or having an aromatic substituent in the o-position to the oxygen atom which joins the phosphorus atom to the aromatic system, or having a fused aromatic system in the o-position to the oxygen atom which joins the phosphorus atom to the aromatic system, $R^2$: aromatic radical having a $C_1$-$C_{18}$-alkyl substituent in the m-position to the oxygen atom which joins the phosphorus atom to the aromatic system, or having an aromatic substituent in the m-position to the oxygen atom which joins the phosphorus atom to the aromatic system, or having a fused aromatic system in the m-position to the oxygen atom which joins the phosphorus atom to the aromatic system, the aromatic radical bearing a hydrogen atom in the o-position to the oxygen atom which joins the phosphorus atom to the aromatic system, $R^3$: aromatic radical having a $C_1$-$C_{18}$-alkyl substituent in the p-position to the oxygen atom which joins the phosphorus atom to the aromatic system, or having an aromatic substituent in the p-position to the oxygen atom which joins the phosphorus atom to the aromatic system, the aromatic radical bearing a hydrogen atom in the o-position to the oxygen atom which joins the phosphorus atom to the aromatic system, $R^4$; aromatic radical which bears substituents other than those defined for $R^1$, $R^2$ and $R^3$ in the o-, m- and p-position to the oxygen atom which joins the phosphorus atom to the aromatic system, the aromatic radical bearing a hydrogen atom in the o-position to the oxygen atom which joins the phosphorus atom to the aromatic system, x: 1 or 2, y,z,p: each independently 0, 1 or 2, with the proviso that x+y+z+p=3.

Preferred phosphites of the formula I b can be taken from DE-A 199 53 058. The $R^1$ radical may advantageously be o-tolyl, o-ethylphenyl, o-n-propylphenyl, o-isopropyl-phenyl, o-n-butylphenyl, o-sec-butylphenyl, o-tert-butylphenyl, (o-phenyl)phenyl or 1-naphthyl groups.

Preferred $R^2$ radicals are m-tolyl, m-ethylphenyl, m-n-propylphenyl, m-isopropylphenyl, m-n-butylphenyl, m-sec-butylphenyl, m-tert-butylphenyl, (m-phenyl)phenyl or 2-naphthyl groups.

Advantageous $R^3$ radicals are p-tolyl, p-ethylphenyl, p-n-propylphenyl, p-isopropyl-phenyl, p-n-butylphenyl, p-sec-butylphenyl, p-tert-butylphenyl or (p-phenyl)phenyl groups.

The $R^4$ radical is preferably phenyl. p is preferably zero. For the indices x, y, z and p in compound I b, there are the following possibilities:

| x | y | z | p |
|---|---|---|---|
| 1 | 0 | 0 | 2 |
| 1 | 0 | 1 | 1 |

-continued

| x | y | z | p |
|---|---|---|---|
| 1 | 1 | 0 | 1 |
| 2 | 0 | 0 | 1 |
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Preferred phosphites of the formula I b are those in which p is zero, and $R^1$, $R^2$ and $R^3$ are each independently selected from o-isopropylphenyl, m-tolyl and p-tolyl, and $R^4$ is phenyl.

Particularly preferred phosphites of the formula I b are those in which $R^1$ is the o-isopropylphenyl radical, $R^2$ is the m-tolyl radical and $R^3$ is the p-tolyl radical with the indices specified in the table above; also those in which $R^1$ is the o-tolyl radical, $R^2$ is the m-tolyl radical and $R^3$ is the p-tolyl radical with the indices specified in the table; additionally those in which $R^1$ is the 1-naphthyl radical, $R^2$ is the m-tolyl radical and $R^3$ is the p-tolyl radical with the indices specified in the table; also those in which $R^1$ is the o-tolyl radical, $R^2$ is the 2-naphthyl radical and $R^3$ is the p-tolyl radical with the indices specified in the table; and finally those in which $R^1$ is the o-isopropylphenyl radical, $R^2$ is the 2-naphthyl radical and $R^3$ is the p-tolyl radical with the indices specified in the table; and also mixtures of these phosphites.

Phosphites of the formula I b may be obtained by
a) reacting a phosphorus trihalide with an alcohol selected from the group consisting of $R^1OH$, $R^2OH$, $R^3OH$ and $R^4OH$ or mixtures thereof to obtain a dihalophosphorous monoester,
b) reacting the dihalophosphorous monoester mentioned with an alcohol selected from the group consisting of $R^1OH$, $R^2OH$, $R^3OH$ and $R^4OH$ or mixtures thereof to obtain a monohalophosphorous diester and
c) reacting the monohalophosphorous diester mentioned with an alcohol selected from the group consisting of $R^1OH$, $R^2OH$, $R^3OH$ and $R^4OH$ or mixtures thereof to obtain a phosphite of the formula I b.

The reaction may be carried out in three separate steps. Equally, two of the three steps may be combined, i.e. a) with b) or b) with c). Alternatively, all of the steps a), b) and c) may be combined together.

Suitable parameters and amounts of the alcohols selected from the group consisting of $R^1OH$, $R^2OH$, $R^3OH$ and $R^4OH$ or mixtures thereof may be determined readily by a few simple preliminary experiments.

Useful phosphorus trihalides are in principle all phosphorus trihalides, preferably those in which the halide used is Cl, Br, I, in particular Cl, and mixtures thereof. It is also possible to use mixtures of various identically or differently halogen-substituted phosphines as the phosphorus trihalide. Particular preference is given to $PCl_3$. Further details on the reaction conditions in the preparation of the phosphites I b and for the workup can be taken from DE-A 199 53 058.

The phosphites I b may also be used in the form of a mixture of different phosphites I b as a ligand. Such a mixture may be obtained, for example, in the preparation of the phosphites I b.

However, preference is given to the phosphorus ligand being multidentate, in particular bidentate. The ligand used therefore preferably has the formula II $$\begin{array}{c} R^{11}-X^{11} \\ \phantom{R^{11}-}\diagdown \\ \phantom{R^{11}-X^{11}}P-X^{13}-Y-X^{23}-P \\ \phantom{R^{11}-}\diagup \\ R^{12}-X^{11} \end{array} \begin{array}{c} X^{21}-R^{21} \\ \diagdown \\ \diagup \\ X^{22}-R^{22} \end{array} \quad (II)$$

where
$X^{11}, X^{12}, X^{13}, X^{21}, X^{22}, X^{23}$ are each independently oxygen or a single bond
$R^{11}, R^{12}$ are each independently identical or different, separate or bridged organic radicals
$R^{21}, R^{22}$ are each independently identical or different, separate or bridged organic radicals,
Y is a bridging group.

In the context of the present invention, compound II is a single compound or a mixture of different compounds of the aforementioned formula.

In a preferred embodiment, $X^{11}$, $X^{12}$, $X^{13}$, $X^{21}$, $X^{22}$, $X^{23}$ may each be oxygen. In such a case, the bridging group Y is bonded to phosphite groups.

In another preferred embodiment, $X^{11}$ and $X^{12}$ may each be oxygen and $X^{13}$ a single bond, or $X^{11}$ and $X^{13}$ oxygen and $X^{12}$ a single bond, so that the phosphorus atom surrounded by $X^{11}$, $X^{12}$ and $X^{13}$ is the central atom of a phosphonite. In such a case, $X^{21}$, $X^{22}$ and $X^{23}$ may be oxygen, or $X^{21}$ and $X^{22}$ may each be oxygen and $X^{23}$ a single bond, or $X^{21}$ and $X^{23}$ may each be oxygen and $X^{22}$ a single bond, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphonite, phosphinite or phosphine, preferably a phosphonite.

In another preferred embodiment, $X^{13}$ may be oxygen and $X^{11}$ and $X^{12}$ each a single bond, or $X^{11}$ may be oxygen and $X^{12}$ and $X^{13}$ each a single bond, so that the phosphorus atom surrounded by $X^{11}$, $X^{12}$ and $X^{13}$ is the central atom of a phosphonite. In such a case, $X^{21}$, $X^{22}$ and $X^{23}$ may each be oxygen, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphinite or phosphine, preferably a phosphinite.

In another preferred embodiment, $X^{11}$, $X^{12}$ and $X^{13}$ may each be a single bond, so that the phosphorus atom surrounded by $X^{11}$, $X^{12}$ and $X^{13}$ is the central atom of a phosphine. In such a case, $X^{21}$, $X^{22}$ and $X^{23}$ may each be oxygen, or $X^{21}$, $X^{22}$ and $X^{23}$ may each be a single bond, so that the phosphorus atom surrounded by $X^{21}$, $X^{22}$ and $X^{23}$ may be the central atom of a phosphite or phosphine, preferably a phosphine.

The bridging group Y is preferably an aryl group which is substituted, for example by $C_1$-$C_4$-alkyl, halogen, such as fluorine, chlorine, bromine, halogenated alkyl, such as trifluoromethyl, aryl, such as phenyl, or is unsubstituted, preferably a group having from 6 to 20 carbon atoms in the aromatic system, in particular pyrocatechol, bis(phenol) or bis(naphthol).

The $R^{11}$ and $R^{12}$ radicals may each independently be identical or different organic radicals. Advantageous $R^{11}$ and $R^{12}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{21}$ and $R^{22}$ radicals may each independently be identical or different organic radicals. Advantageous $R^{21}$ and $R^{22}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{11}$ and $R^{12}$ radicals may each be separate or bridged. The $R^{21}$ and $R^{22}$ radicals may also each be separate or bridged. The $R^{11}$, $R^{12}$, $R^{21}$ and $R^{22}$ radicals may each be separate, two may be bridged and two separate, or all four may be bridged, in the manner described.

In a particularly preferred embodiment, useful compounds are those of the formula I, II, III, IV and V specified in U.S. Pat. No. 5,723,641. In a particularly preferred embodiment, useful compounds are those of the formula I, II, III, IV, V, VI and VII specified in U.S. Pat. No. 5,512,696, in particular the compounds used there in examples 1 to 31. In a particularly preferred embodiment, useful compounds are those of the formula I, II, III, IV, V, VI, VII, VIII, IX, X, XI, XII, XIII, XIV and XV specified in U.S. Pat. No. 5,821,378, in particular the compounds used there in examples 1 to 73.

In a particularly preferred embodiment, useful compounds are those of the formula I, II, III, IV, V and VI specified in U.S. Pat. No. 5,512,695, in particular the compounds used there in examples 1 to 6. In a particularly preferred embodiment, useful compounds are those of the formula I, II, III, IV, V, VI, VII, VII, IX, X, XI, XII, XII and XIV specified in U.S. Pat. No. 5,981,772, in particular the compounds used there in examples 1 to 66.

In a particularly preferred embodiment, useful compounds are those specified in U.S. Pat. No. 6,127,567 and the compounds used there in examples 1 to 29. In a particularly preferred embodiment, useful compounds are those of the formula I, II, III, IV, V, VI, VII, VII, IX and X specified in U.S. Pat. No. 6,020,516, in particular the compounds used there in examples 1 to 33. In a particularly preferred embodiment, useful compounds are those specified in U.S. Pat. No. 5,959,135, and the compounds used there in examples 1 to 13.

In a particularly preferred embodiment, useful compounds are those of the formula I, II and III specified in U.S. Pat. No. 5,847,191. In a particularly preferred embodiment, useful compounds are those specified in U.S. Pat. No. 5,523,453, in particular the compounds illustrated there in formula 1, 2, 3, 4, 5, 6, 7, 8, 9, 10, 11, 12, 13, 14, 15, 16, 17, 18, 19, and 21. In a particularly preferred embodiment, useful compounds are those specified in WO 01/14392, preferably the compounds illustrated there in formula V, VI, VII, VIII, IX, X, XI, XII, XIII, XIV, XV, XVI, XVII, XXI, XXII, XXIII.

In a particularly preferred embodiment, useful compounds are those specified in WO 98/27054. In a particularly preferred embodiment, useful compounds are those specified in WO 99/13983. In a particularly preferred embodiment, useful compounds are those specified in WO 99/64155.

In a particularly preferred embodiment, useful compounds are those specified in the German patent application DE 100 380 37. In a particularly preferred embodiment, useful compounds are those specified in the German patent application DE 100 460 25. In a particularly preferred embodiment, useful compounds are those specified in the German patent application DE 101 502 85.

In a particularly preferred embodiment, useful compounds are those specified in the German patent application DE 101 502 86. In a particularly preferred embodiment, useful compounds are those specified in the German patent application DE 102 071 65. In a further particularly preferred embodiment of the present invention, useful phosphorus chelate ligands are those specified in US 2003/0100442 A1.

In a further particularly preferred embodiment of the present invention, useful phosphorus chelate ligands are those specified in the German patent application reference no. DE 103 50 999.2 of Oct. 30, 2003, which has an earlier priority date but was unpublished at the priority date of the present application.

The compounds I, I a, I b and II described and their preparation are known per se. Phosphorus ligands used may also be mixtures comprising at least two of the compounds I, I a, I b and II.

In a particularly preferred embodiment of the process according to the invention, the phosphorus ligand of the nickel(0) complex and/or the free phosphorus ligand is selected from tritolyl phosphite, bidentate phosphorus chelate ligands and the phosphites of the formula I b

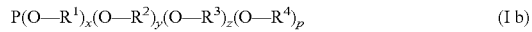

(I b)

where $R^1$, $R^2$ and $R^3$ are each independently selected from o-isopropylphenyl, m-tolyl and p-tolyl, $R^4$ is phenyl; x is 1 or 2, and y, z, p are each independently 0, 1 or 2 with the proviso that x+y+z+p=3; and mixtures thereof.

The hydrocyanation is preferably carried out at pressures of from 0.1 to 500 MPa, more preferably from 0.5 to 50 MPa, in particular from 1 to 5 MPa. The reaction is preferably carried out at temperatures of from 273 to 473 K, more preferably from 313 to 423 K, in particular from 333 to 393 K. Advantageous average mean residence times of the liquid reactor phase have been found to be in the range from 0.001 to 100 hours, preferably from 0.05 to 20 hours, more preferably from 0.1 to 5 hours, per reactor. 1,3-Butadiene may be metered in a molar ratio of 1:1 in relation to hydrogen cyanide, based on the sum of all feeds of the reactor battery. However, preference is given to running the reaction by metering 1,3-butadiene in such a way that the molar ratios between 1,3-butadiene and hydrogen cyanide are in the range from 1.6:1 to 1.1:1, more preferably from 1.6:1 to 1.3:1, as described in DE-A-102 004 004 696. In the case of division of the hydrogen cyanide into equal parts to a plurality of reactors, this results, viewed for the individual reactor, in higher excesses of 1,3-butadiene, which are not ruled out by the above specifications.

The loop reactor is preferably designed in such a size that the residual content of hydrogen cyanide in the effluent stream from the loop reactor is less than 10% by weight, more preferably less than 5% by weight, in particular from 1% by weight, based on the mass of the effluent stream. These specifications apply for the target conversions based on 1,3-butadiene, preferably also for lower conversions than the target conversion when the catalyst is partly deactivated.

Owing to the short mixing-in times and the associated low degree of local excess concentrations of hydrogen cyanide, preference is given to using a loop reactor in a process for preparing 3-pentenenitrile. This reduces the nickel cyanide formation rate relative to the product formation rate. In addition, the energy of reaction can be readily removed from the present system, since the loop reactor is equipped in accordance with the invention with at least one heat transferrer in the external circulation system.

WORKING EXAMPLES

Working examples hereinbelow show, by way of example, the advantage of jet loop reactors with regard to the low outlet concentration of hydrogen cyanide.

In all examples, a jet loop reactor having a capacity of 12 l is used. The internal tube has a diameter of 50 mm and a length of 1.4 m. The pumped circulation system consists of a pump and a heat transferrer which is used as a cooler for removing the heat of reaction. The apparatus and the line of the pumped circuit have a volume together of 20 l.

Hydrogen cyanide is sprayed through a driving jet nozzle, cooled to 0° C., at the top of the vertical loop reactor; 1,3-butadiene and the catalyst stream are introduced into the pumped circuit at a temperature of 100° C. The product stream is withdrawn from the outer edge of the internal circulation system at about 75% of the height of the reactor. The pumped circulation stream is drawn off at the lower end of the reactor and fed back in via the nozzle. Between these two points, a temperature differential is measured, which is a measure of the reaction rate in the interior of the loop reactor. The temperature at the lower outlet of the reactor is controlled by the removal of heat in the external cooler.

The stabilizing ligand of the nickel(0) complex used is a mixture of the chelate ligand 1 and tri-m/p-tolyl phosphite. The catalyst solution is obtained by mixing 40 kg of a mixture having 2.3% by weight of nickel(0), 15% by weight of 3-pentenenitrile and a remainder of tri-m/p-tolyl phosphite with 104 kg of another mixture having 23.1% of the ligand 1 and the remainder of 3-pentenenitrile to obtain a solution which is referred to hereinbelow as catalyst solution.

From the effluent stream from the loop reactor, samples are taken. Absorption of the hydrogen cyanide in aqueous sodium hydroxide solution cooled to 0° C. quantitatively removes the hydrogen cyanide content of the stream which is determined by immediately subsequent titration of the sodium hydroxide solution.

Abbreviations:
HCN=Hydrogen cyanide
BD=1,3-Butadiene
CAT=Catalyst solution
ΔT=Temperature differential between pumped circulation stream withdrawal point and pumped circulation stream feed point.

Example 1

7.5 kg/h of HCN are fed to the reactor; 18.0 kg/h of BD and 11.7 kg/h of CAT are metered into the pumped circuit. A product stream of 37.2 kg/h is obtained. After a running time of 48 h, ΔT is 4 K. The analysis at this time gives a content of HCN in the effluent stream of 90 ppm by weight.

This example illustrates the low HCN concentration which arises in the product stream to be worked up. The conversion of butadiene is high in comparison to Example 2.

Example 2

7.5 kg/h of HCN are fed to the reactor; 18.0 kg/h of BD and 2.6 kg/h of CAT are metered into the pumped circuit. A product stream of 28.1 kg/h is obtained. After a running time of 46 h, ΔT is 2 K. The analysis at this time gives a content of HCN in the effluent stream of 1470 ppm by weight.

This example illustrates that, even at lower conversion which arises from the higher catalyst hourly space velocity than in Example 1, the product stream to be worked up only contains a small amount of HCN.

Example 3

7.5 kg/h of HCN are fed to the reactor; 21.0 kg/h of BD and 31.7 kg/h of CAT are metered into the pumped circuit. A product stream of 60.2 kg/h is obtained. After leaving the reactor, the effluent stream was subjected to a workup as described in Example 1 of DE-A-102 004 004 724. The catalyst recycle stream obtained was recycled without discharge and fresh catalyst supplementation in the above-described amount. The amount of butadiene also contains a butadiene recycled in this way which has been supplemented by the appropriate amount of fresh butadiene needed.

After a running time of 2 h, ΔT is 5.5 K. The analysis at this time gives a content of HCN in the effluent stream of less than 10 ppm by weight. After a running time of 126 h, ΔT is 2.5 K. The analysis at this time gives a content of HCN in the effluent stream of 2260 ppm by weight.

The example shows that even when conversion is falling owing to catalyst deactivation in a closed catalyst cycle, the HCN content in the product stream to be worked out remains low.

What is claimed is:

1. A process for preparing 3-pentenenitrile by hydrocyanating 1,3-butadiene in the presence of at least one Ni(0) catalyst comprising phosphorus ligands selected from mono- and bidentate phosphines, phosphites, phosphinites and phosphonites, the process comprising conducting the hydrocyanation in a loop reactor having at least one feed line and at least one discharge line, an external pumped circulation system, an inlet tube and at least one jet nozzle for driving the internal circulation.

2. The process according to claim 1, wherein the hydrocyanation is conducted continuously.

3. The process according to claim 1, wherein the hydrocyanation is conducted in the liquid phase.

4. The process according to claim 1, wherein the loop reactor is in flooded operation.

5. The process according to claim 1, further comprising using one or more additional reactors for the hydrocyanation in addition to the loop reactor, in which case at least two reactors are connected in series, hydrogen cyanide is introduced into more than one reactor, and 1,3-butadiene and the at least one catalyst are introduced into the first of the reactors connected in series.

6. The process according to claim 1, further comprising adding hydrogen cyanide to the loop reactor in an internal inlet tube and the pumped circulation stream is conducted coaxially around this inlet tube.

7. The process according to claim 1, wherein 3-pentenenitrile is withdrawn at the point in the loop reactor where the internal circulation stream has the longest circulation time before the mixing with the driving jet.

8. The process according to claim 1, wherein the 1,3-butadiene or the at least one catalyst are metered into the external pumped circulation system.

9. The process according to claim 1, further comprising cooling the inlet point for metering the hydrogen cyanide.

10. The process according to claim 1, further comprising providing a postreactor having tubular characteristics connected downstream of the loop reactor.

11. The process according to claim 6, wherein 3-pentenenitrile is withdrawn at the point in the loop reactor where the internal circulation stream has the longest circulation time before the mixing with the driving jet.

12. The process according to claim 11, further comprising cooling the inlet point for metering the hydrogen cyanide.

13. The process according to claim 12, further comprising providing a postreactor having tubular characteristics connected downstream of the loop reactor.

* * * * *